United States Patent [19]

Wong

[11] Patent Number: 4,578,762
[45] Date of Patent: Mar. 25, 1986

[54] SELF-CALIBRATING CARBON DIOXIDE ANALYZER

[75] Inventor: Jacob Y. Wong, Santa Barbara, Calif.

[73] Assignee: Tri-Med Inc., Bellevue, Wash.

[21] Appl. No.: 509,920

[22] Filed: Jul. 1, 1983

[51] Int. Cl.$^4$ .................. G06F 15/46; G01N 21/26
[52] U.S. Cl. ...................................... 364/497; 128/719; 250/343; 356/437; 364/571; 422/83
[58] Field of Search ................ 364/496–499, 364/571; 250/343–345, 347–351, 353; 422/62, 83, 84, 88, 89, 92, 98, 119; 436/900; 128/719, 205.28, 205.29; 356/51, 437, 243

[56] References Cited

U.S. PATENT DOCUMENTS

| | | | |
|---|---|---|---|
| 3,793,525 | 2/1974 | Burch et al. | 250/343 |
| 3,811,776 | 5/1974 | Blau, Jr. | 356/51 |
| 3,821,553 | 6/1974 | French | 250/345 X |
| 3,878,107 | 4/1975 | Pembrook et al. | 250/343 |
| 4,204,768 | 5/1980 | N'Guyen | 250/343 X |
| 4,345,840 | 8/1982 | Goetz et al. | 356/51 X |
| 4,371,785 | 2/1983 | Pedersen | 250/343 |

OTHER PUBLICATIONS

Solomon—"A Reliable Accurate CO$_2$ Analyzer for Medical Use"—Hewlett-Packard Journal, Sep. 1981-pp. 3-21.

*Primary Examiner*—Joseph Ruggiero
*Attorney, Agent, or Firm*—Harry W. Brelsford

[57] ABSTRACT

A carbon dioxide analyzer for medical purposes is rendered self-calibrating by continuously measuring pairs of two or three each of several components as follows:

1st pair: vacuum cell, open hole and sample cell reference cell, open hole and sample cell
2nd pair: vacuum cell, standard cell reference cell, standard cell
3rd pair: vacuum cell, open hole reference cell, open hole
4th pair: vacuum cell, standard cell, sample cell reference cell, standard cell, sample cell The ratios of these measurement pairs are treated mathematically in a computer or microprocessor to obtain a reading for CO$_2$ and to correct other readings and to monitor the integrity of the standard cell. A novel two-wheel chopper and mirror arrangement facilitates the measurements.

10 Claims, 30 Drawing Figures

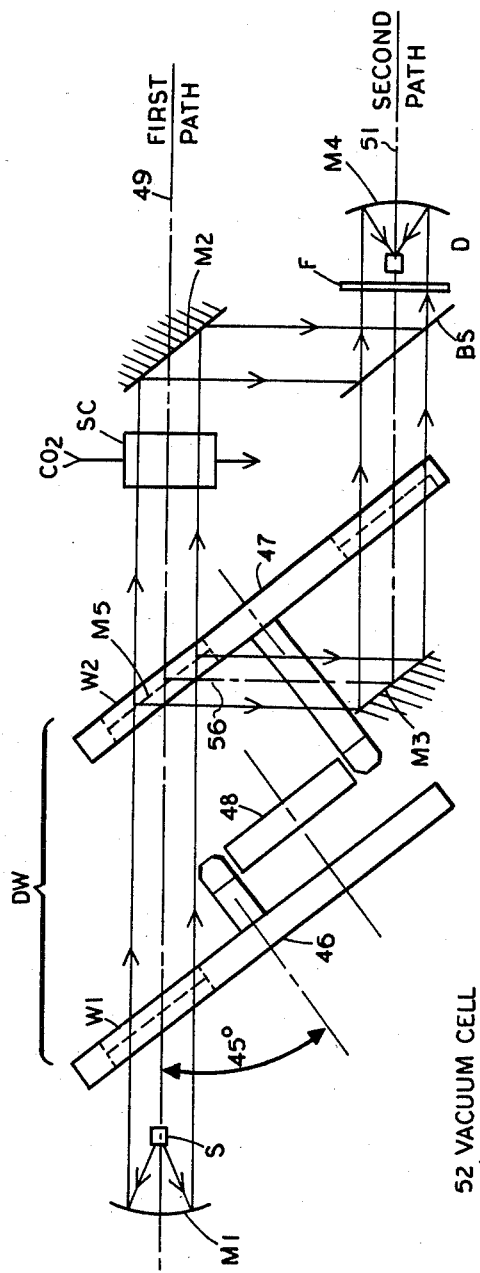
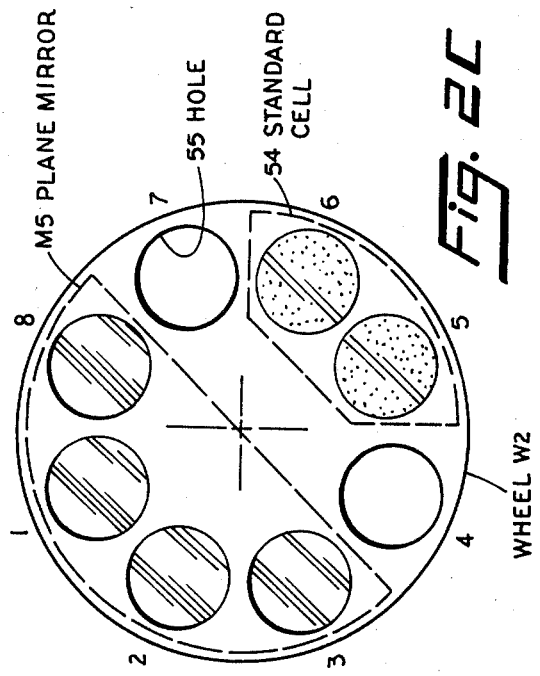
Fig. 2A
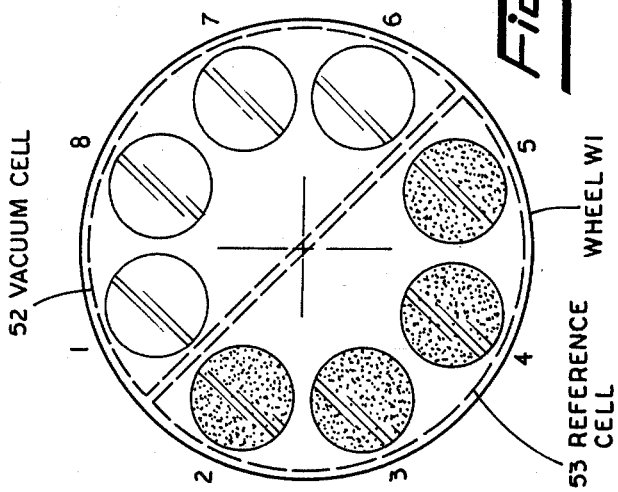
Fig. 2B
Fig. 2C

| MEASUREMENT NUMBERS | FUNCTION | WHEEL NO. 1 | | WHEEL NO. 2 | | MEASUREMENT | | REMARKS |
|---|---|---|---|---|---|---|---|---|
| | | POSITION | COMPONENT | POSITION | COMPONENT | SAMPLE CELL | | |
| 1 | $CO_2$ measurement in the sample chamber | 7 | VACUUM CELL | 7 | OPEN HOLE | IN | $V_S$ | SEE FIGURE 4 |
| 2 | | 4 | REFERENCE CELL | 4 | OPEN HOLE | IN | $V_R$ | $Q, Q_0, Q_1$ |
| 3 | $CO_2$ measurement in the Standard Cell | 1 | VACUUM CELL | 1 | STANDARD CELL | OUT | $V'_S$ | SEE FIGURE 5 |
| 4 | | 2 | REFERENCE CELL | 2 | STANDARD CELL | OUT | $V'_R$ | $Q_S$ |
| 5 | $CO_2$ measurement inside instrument sensor compartment | 8 | VACUUM CELL | 8 | OPEN HOLE | OUT | $V''_S$ | SEE FIGURE 6 |
| 6 | | 3 | REFERENCE CELL | 3 | OPEN HOLE | OUT | $V''_R$ | $Q_A$ |
| 7 | Monitor $CO_2$ conc. in Standard Cell | 6 | VACUUM CELL | 6 | STANDARD CELL | IN | $V^o_S$ | SEE FIGURE 7 |
| 8 | | 5 | REFERENCE CELL | 5 | STANDARD CELL | IN | $V^o_R$ | $Q_I$ |

Fig. 3

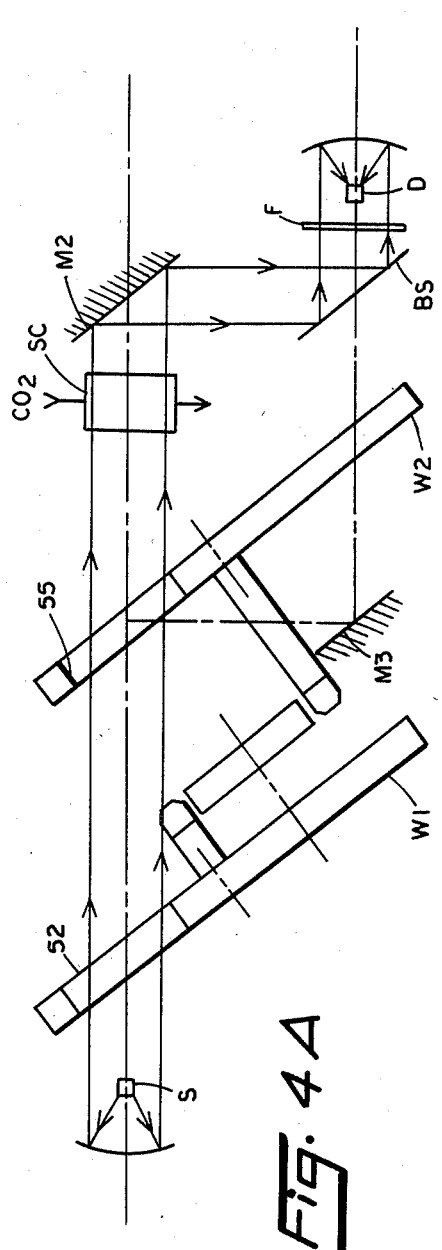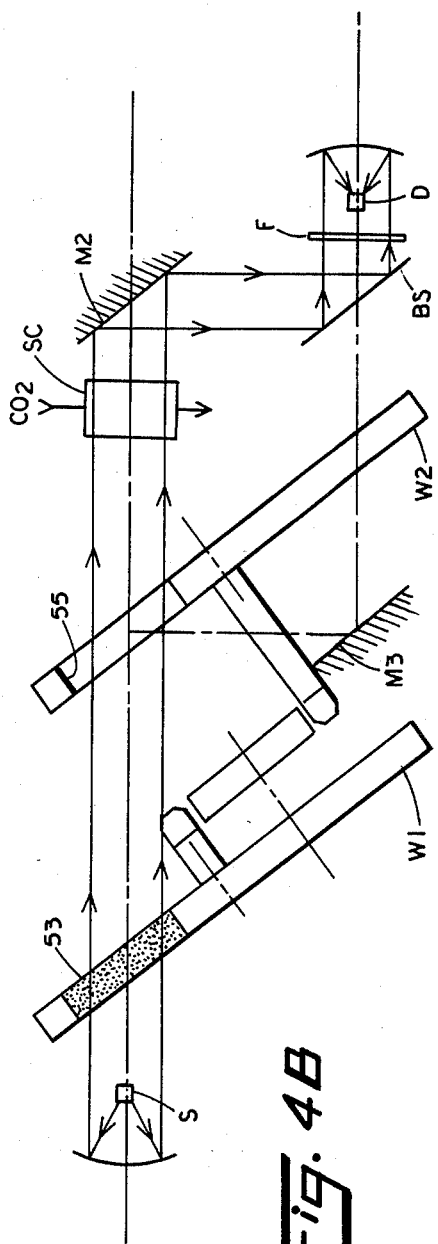
Fig. 4A
Fig. 4B

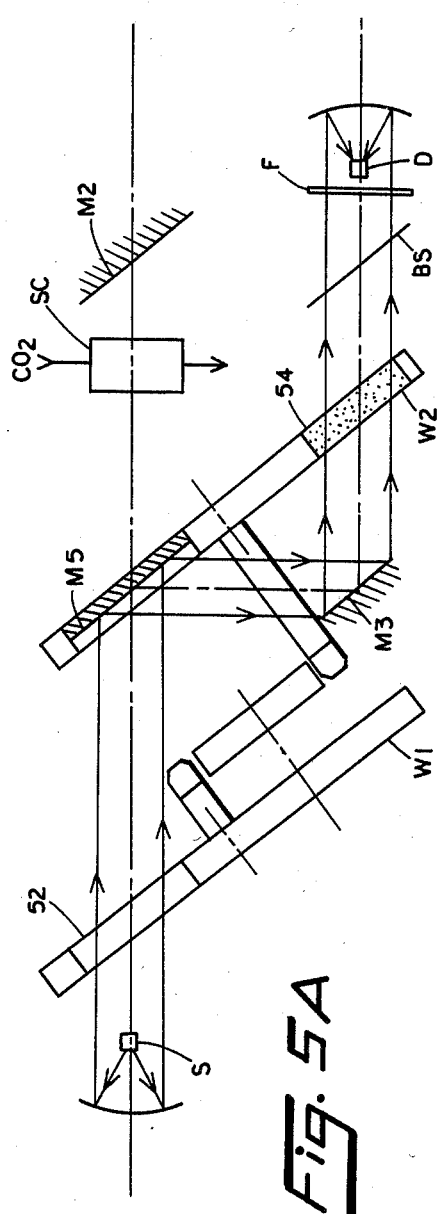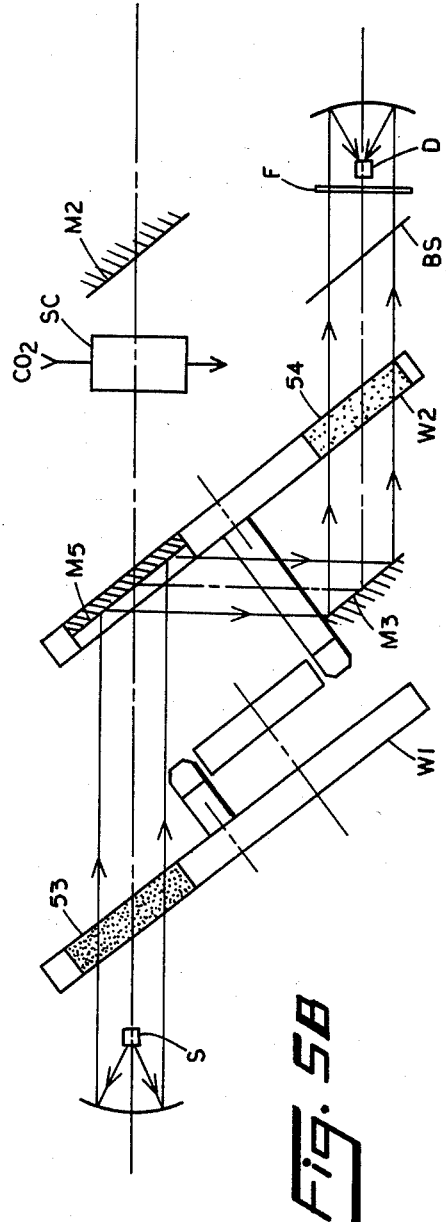
Fig. 5A
Fig. 5B

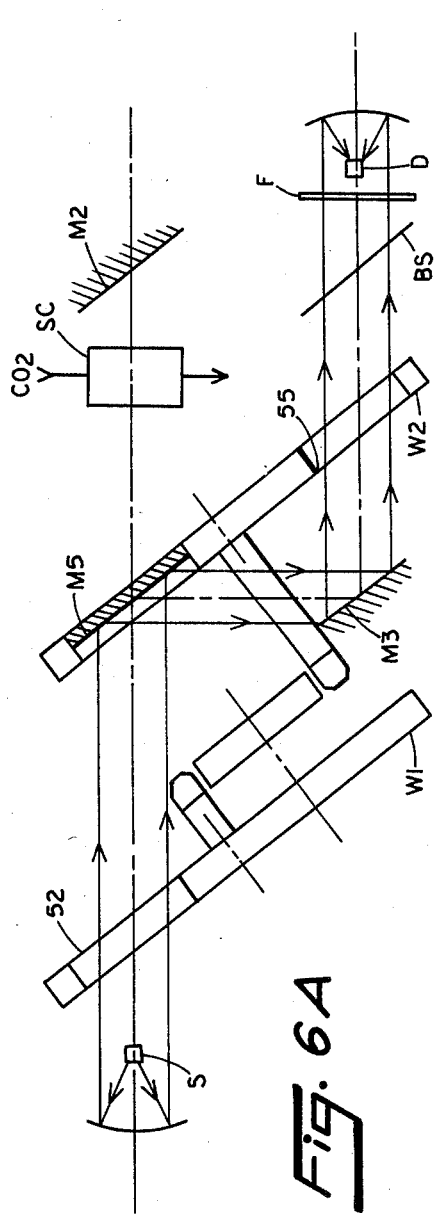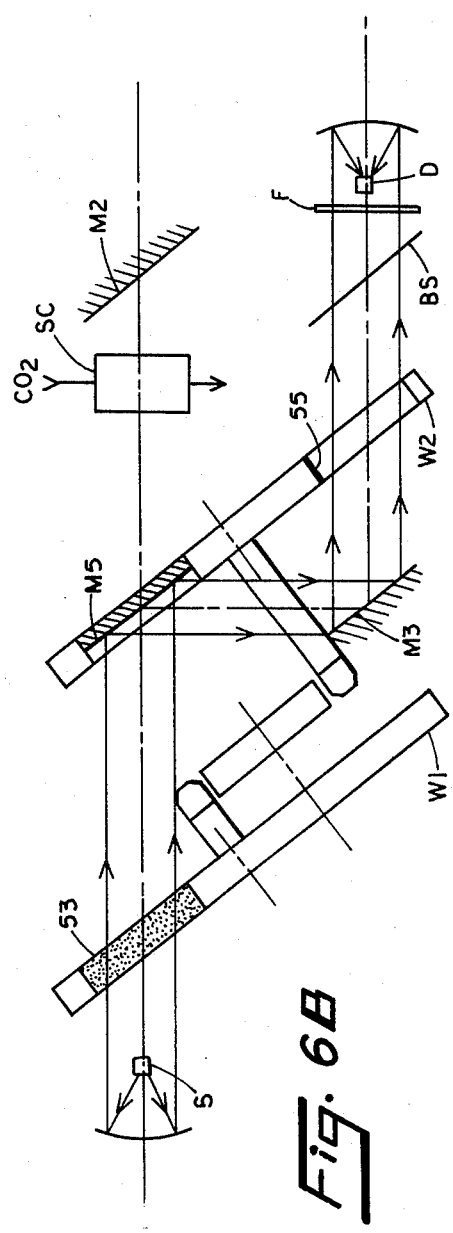

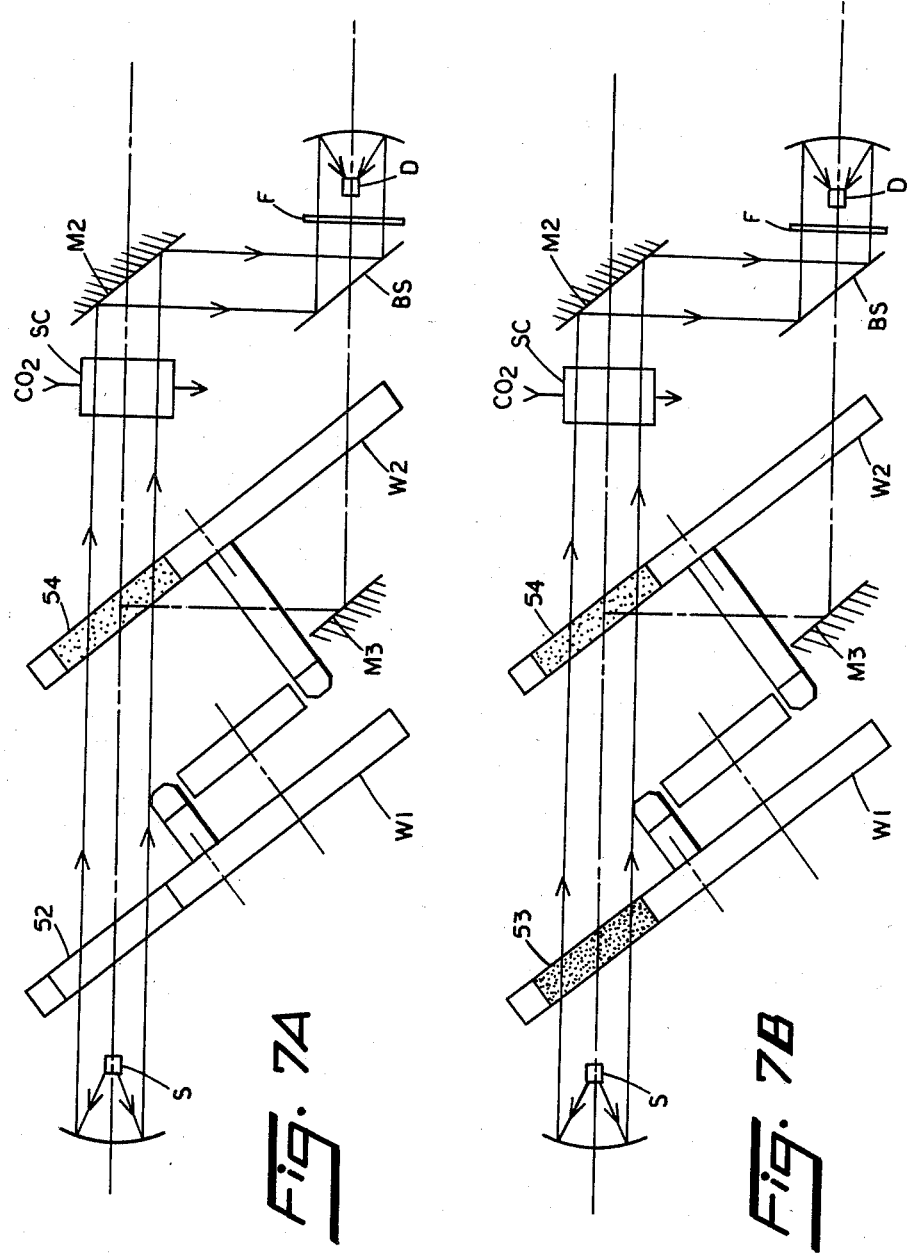

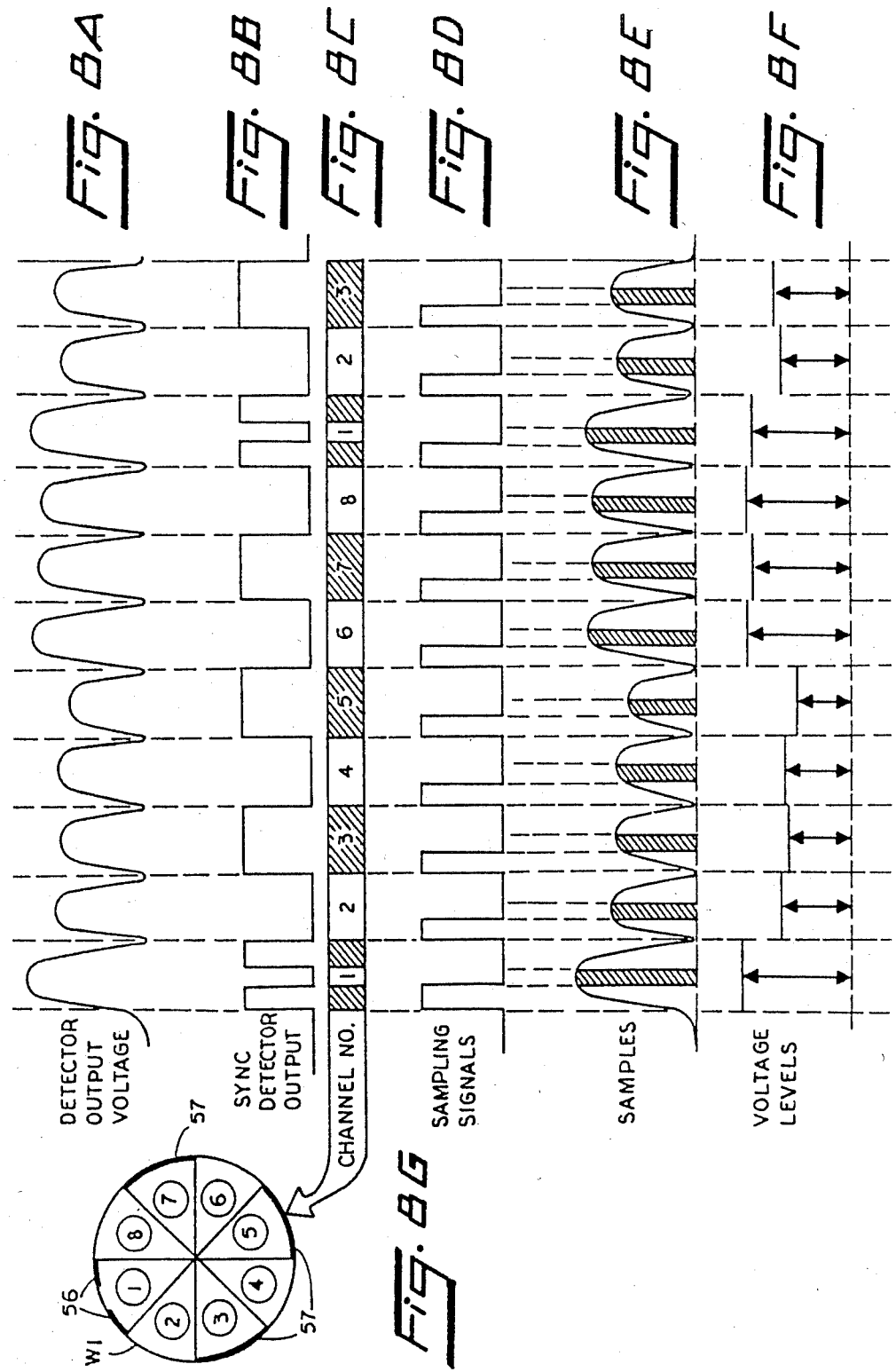

SELF-CALIBRATING CARBON DIOXIDE ANALYZER

TECHNICAL FIELD

This invention relates to the quantitative measurement of the concentration of a particular gas in a gas mixture using the principle of non-linear absorption, by the gas to be measured, of particular wavelengths in the electromagnetic spectrum; for example, in the region of infrared. The invention provides apparatus and method for such measurements wherein the apparatus is continuously self-calibrating regardless of various temporal or environmental changes that can occur in the apparatus during normal operation and from time to time.

BACKGROUND OF THE PRIOR ART

This invention will be described as applied to the measurement the carbon dioxide ($CO_2$). Such measurement apparatus is generally referred to as a gas analyzer and will be described as a carbon dioxide analyzer. The non-dispersive infrared technique utilizing the 4.26 microns absorption band of $CO_2$ has been widely used in the gas analyzer industry for the detection of this gas. The term "non-dispersive" refers to the use of spectral band-pass filtering. This technique offers a number of advantages including speed of response and greater sensitivity over older methods that used the principle of heat transfer based upon radiation absorption by $CO_2$. However, this non-dispersive infrared technique is not immune to instrument zero and span drifts due to changes incomponent characteristics caused by either aging or externally induced stimuli. Furthermore, this method does not automatically exploit the other implicit advantages of this technique in achieving instrument stability, interference rejection by other absorbing gases, and ease of recalibration.

NEGATIVE FILTERING

These inherent advantages of the non-dispersive infrared method can be realized by a technique known in the industry as "Negative Filtering" which combines $CO_2$ prefiltering or preabsorption and two-beam ratioing. In this technique two measuring conditions are set up. In the first measuring condition, shown in FIG. A, also known as the "sample" beam, radiation from a blackbody source S is made to traverse a transparent "vacuum" cell V (or a cell that does not contain $CO_2$ gas) before passing through the sample chamber SC. The radiation then traverses the interference band-pass filter F which spectrally limits the radiation before reaching the detector D, preferably a photodetector such as a PbSe photoconductor. The voltage transduced by the detector in this configuration is usually referred to as $V_S$, meaning the voltage resulting from the beam traversing a vacuum cell and the sample chamber.

In the second measuring condition shown in FIG. B, also known as the "reference" beam, radiation or light traverses a reference cell R containing a known concentrated amount of $CO_2$ before passing through the sample chamber. The light then traverses the interference band-pass filter before reaching the PbSe detector. The transduced voltage by the detector in this configuration is $V_R$, meaning the voltage due to infrared radiation passing through the reference cell and the sample chamber.

In the third measuring condition shown in FIG. C radiation traverses a hole before passing through the sample chamber. The light then traverses the interference band-pass filter before reaching the PbSe detector. The transduced voltage by the detector in this configuration is $V_H$, meaning the voltage due to the infrared radiation passing through the hole and the sample chamber.

THE RATIO $V_R/V_S$ IS DESIGNATED AS "Q"

The voltage ratio $V_R/V_S$ is used to relate the $CO_2$ gas present in the sample chamber and is usually designated as Q. Because of the non-linearity of $CO_2$ gas absorption at 4.26 microns, $V_S$ decreases much faster than $V_R$ as a function of $CO_2$ gas present in the sample chamber. This relationship is shown in FIG. D. This is because in the "reference" beam the reference cell takes out most of the energy contained in the interference filter pass-band prior to its reaching the sample chamber. Thus, any additional $CO_2$ present in the sample chamber does not significantly alter this beam intensity. On the other hand, in the "sample" beam the transduced voltage $V_S$ varies more strongly with the $CO_2$ gas present in the sample chamber (compared to $V_R$). This is because no absorption takes place in the vacuum cell, which does not contain $CO_2$ gas. The ratio $V_R/V_S$ therefore varies as a function of $CO_2$ level in the sample chamber.

The ratio $V_R/V_S$ or Q is used to correlate the measured $CO_2$ gas because of the fact that any nonspectral variation that is present in the beam would appear to the detector to be the same for both beams leading to substantial cancellation of the variation as seen by the detector. These variations could be due to changes in any of the optical components of the system. For spectrally-related variations such as absorption by interfering gases or change in the spectral characteristics for the source, filter, detector, etc., the cancellation is only operative to first order. Second or higher order corrections are not operative even if the ratio $V_R/V_S$ is used to relate the $CO_2$ concentration in the sample chamber with the calibration curve. Thus, by using a "Negative Filtering" technique, most first order effects caused by changes in the optical components such as aging or by external stimuli are cancelled leading to a stable and accurate $CO_2$ measurement method.

THE RATIO $V_R/V_H$ IS DESIGNATED AS "U"

Referring to FIGS. B and C, the voltage ratio $V_R/V_H$ is used to monitor the $CO_2$ gas level inside the sensor head or in the spaces between the various optical components from S to D. In order for the voltage ratio $Q=V_R/V_S$ to correctly relate the $CO_2$ gas present in the sample chamber, as discussed previously, this $CO_2$ level inside the sensor head must in practice be very low (2 mmHg or less). When this $CO_2$ level is very nearly zero the $V_H$ curve (see FIG. D) is almost identical (except for certain aperture effects due to different geometrical sizes which might be present) to the $V_S$ curve and the ratio U-curve follows closely to the ratio Q-curve as depicted in FIG. D. However, when the $CO_2$ level inside the sensor head starts to build up in quantity the output $V_{H'}$ (corresponding to the measurement arrangement shown in FIG. C) deviates substantially from $V_S$ and the ratio U'-curve ($U'=V_R/V_{H'}$) is no longer the same as the original Q-curve (see FIG. D). Significant error will result in the measurement of $CO_2$ gas present in the sample chamber if the user is not warned of such a circumstance. The U-curve is used to provide such a warning signal to the user should its difference from the original Q-curve exceeds a certain predetermined value.

DOUBLE-Q NEGATIVE FILTERING METHOD

Instead of using the voltage ratio $V_R/V_S$ or Q to relate the $CO_2$ gas present in the sample chamber a superior method commonly known to the gas analyzer industry as the Double-Q Negative Filtering technique is preferred. With the selection of proper design values for the optical components used in the instrument such as in the case of the Hewlett-Packard Capnometer this technique requires for recalibration the matching of only two points (commonly taken to be at 0 mmHg and 55 mmHg) on the calibration curve for adequately restoring the original performance accuracy for the instrument. In this technique two initial calibration constants $Q_0$ and $Q_1$ are specially created for subsequent signal processing use. $Q_0$ is defined as the value of $Q=V_R/V_S$ when there is zero $CO_2$ present in the sample chamber. $Q_1$ is defined as the value of Q when there is 55 mmHg of $CO_2$ present in the sample chamber.

Both $Q_0$ and $Q_1$ are determined experimentally in the beginning and stored away in non-volatile EAROM-(Electrically Alterable Read Only Memory) in the computer section of the instrument. They are so stored in order that their values can be quickly retrieved by the microprocessor which is part of the instrument for computing the $CO_2$ value in the sample chamber based upon the measured value of Q. Furthermore, both $Q_0$ and $Q_1$ values can be periodically checked for changes with the use of a zero $CO_2$ standard (for $Q_0$) and a 55 mmHg $CO_2$ standard (for $Q_1$) in place of the sample chamber as practiced presently in the Hewlett-Packard Capnometer. The changes in $Q_0$ and $Q_1$ values, if any, reflect the component changes inside the instrument caused by either aging or external stimuli. If these changes exceed a certain predetermined limit they can be applied to the original values for $Q_0$ and $Q_1$ thereby generating new $Q_0$ and $Q_1$ values. The fact that the original $Q_0$ and $Q_1$ values are stored in EAROM and not in the permanent memory (Read Only Memory) of the microprocessor enables the user to instruct the instrument to store these new values in place of the old ones. The new or updated $Q_0$ and $Q_1$ values continue to be stored in EAROM for further updating if needed in the future. These new values of $Q_0$ and $Q_1$ adequately restore the measurement accuracy for the instrument as so adeptly demonstrated in the current Hewlett-Packard Capnometer.

HOW THE DOUBLE-Q METHOD WORKS

The two-point recalibration routine described in the above section and afforded by the Double-Q technique is the direct result of using a new parameter called S (to be defined later) instead of Q in the calibration curve of the instrument. The former is called a calibration S-curve and the latter a calibration Q-curve.

The $pCO_2$ in the sample chamber is represented by the calibration Q-curve in the form:

$$pCO_2(mmHg) = B_0 + B_1 Q + B_2 Q^2$$

where $$Q = V_R/V_S$$

and $B_0$, $B_1$ and $B_2$ are coefficient constants empirically determined by fitting a large number of experimental data points linking $pCO_2$ levels in the sample chamber to the measured Q values.

The $pCO_2$ in the sample chamber is represented by the calibration S-curve in the form:

$$pCO_2(mmHg) = A_0 + A_1 S + A_2 S^2$$

where S is defined as $$S = (Q - Q_0)/(Q_1 - Q_0)$$

where $Q_0$ and $Q_1$ are given by $$Q_0 = \left. \frac{V_R}{V_S} \right|_{0 \text{ mmHg}}$$

and $$Q_1 = \left. \frac{V_R}{V_S} \right|_{55 \text{ mmHg}}$$

as discussed previously. The quantities $A_0$, $A_1$ and $A_2$ are coefficient constants empirically determined based upon the experimental calibration curve of the instrument, namely, $pCO_2$ in the sample chamber versus the measured values of Q with the use of the calibration constants $Q_0$ and $Q_1$ as defined above. The quantities $A_0$, $A_1$ and $A_2$ are stored in the permanent memory (ROM) section of the microprocessor and their values therefore do not change with time. The quantities $Q_0$ and $Q_1$ are stored on the other hand in EAROM and can be updated in time to reflect any changes in the operating characteristics of the instrument. Since the instrument is basically set up to measure Q (see FIGS. A and B) any changes occurring inside the instrument due to component aging or external stimuli will be reflected in the changes in measured Q values. If the $pCO_2$ in the sample chamber is represented by a calibration Q-curve, the $pCO_2$ value will change leading to a measurement error. This is equivalent of saying that the original calibration curve has shifted. There is no simple way to restore the original calibration Q-curve except to recalibrate the instrument afresh by taking many data points relating the $pCO_2$ values in the sample chamber to Q values and redetermine a new set of coefficint constants $B_0$, $B_1$ and $B_2$.

However, if the $pCO_2$ in the sample chamber is represented by a calibration S-curve the same internal instrument changes which cause Q to change will also change the values of $Q_0$ and $Q_1$. It had been demonstrated (for example in the Hewlett-Packard Capnometer) that in order to adequately restore the original calibration S-curve in this case only the values of $Q_0$ and $Q_1$ need be updated without having to redetermine a new set of $A_0$, $A_1$ and $A_2$ values. This is apparent from the definition of S. The change in Q due to instrument aging or external stimuli for the same $pCO_2$ value in the sample chamber is counteracted by similar changes in $Q_0$ and $Q_1$ so as to render the S value substantially unchanged. Since the set of $A_0$, $A_1$ and $A_2$ values remains unchanged (stored in ROM) the end result is that there will be negligible error in $pCO_2$ measurement despite the change in Q as long as the simultaneous changes in $Q_0$ and $Q_1$ are noted and corrected.

BRIEF DESCRIPTION OF THE INVENTION

The principal drawback of these prior art gas analyzers using negative filtering has been the operation to calibrate the instrument to give an effective zero reading when no $CO_2$ is present in the sample chamber and to give an effective reading when a certain concentration is present. This has been done manually by substituting a vacuum cell for the sample chamber for an effective zero reading, and substituting a sealed vial of known gas concentration for the sample chamber to get calibration for that standard concentration of gas. The present invention avoids this necessity for manual calibration, and provides a gas analyzer that is continuously self-calibrating during normal operation.

Apparatus embodying the invention eliminates the need to periodically check the performance accuracy of the instrument and, in the event that the instrument is found to be operating out of performance specifications, eliminates the need to manually perform the recalibration routine in order to restore its performance accuracy. The current invention renders the carbon dioxide analyzer continuously self-calibrating under normal operating conditions.

Another major improvement afforded by the present invention is the elimination of a relatively long warm-up time (typically 2-5 minutes) after initial instrument turn-on or during manual recalibration prior to the instrument's accuracy being assured. Because of the continuously self-calibrating feature of the instrument provided by the present invention the warm-up time is significantly reduced to less than 30 seconds.

A further advantage of the current invention is the elimination of the need for a "zero" gas standard (commonly taken to be a sapphire blank) during the course of recalibration, thus reducing the cost of the instrument.

It is a further object of the current invention to provide means for continuously checking the integrity of the calibration standard, which takes the form of a hermetically sealed transparent cell containing a predetermined amount of $CO_2$ gas such as 55 mmHg of $CO_2$. Such a means is currently not available in prior art. This is important in view of the fact that the absolute accuracy of the instrument depends upon the gas standard being leak-tight. A continuous means for checking this standard cell for leakage guarantees recalibration accuracy.

It is a further object of the current invention to eliminate the need to standardize the value of $pCO_2$ used in the "span" standard cell wherein $pCO_2$ denotes the partial pressure of $CO_2$ concentration. When the standard cell is used externally for recalibration purposes such as in the case of present day commercial $CO_2$ analyzers this standard cell tends to be intermixed with other sensor heads and instruments. Normally there is one sensor head associated with each carbon dioxide analyzer or instrument. Each carbon dioxide commercial analyzer in turn stores one standard cell for recalibration use. However, situation may arise such that different sensor heads are used with different instruments, and vice versa. Since the same zero and standard values of $CO_2$ have to be used in all present calibration analyzers the result is that each and every standard cell stored in different instruments must have the same $pCO_2$ value. The values for these standard cells may of course differ slightly but the difference directly translates into a recalibration inaccuracy for all instruments. The current invention eliminates this need of exact standardizing of all the standard cells; i.e., they need not have the same $pCO_2$ value. This greatly reduces the effective cost for these standard cells as a much larger percent of the manufactured standard cells can be used due to the tolerance relaxation in $pCO_2$ value.

BRIEF DESCRIPTION OF THE INVENTION APPARATUS

The current invention comprises a combination of a unique dualwheel optical system design and a special calibration methodology.

The special calibration methodology provides a mathematical formalism for effectively restoring the original calibration curve of the instruments by linking the outputs of two internal standards to system changes detected. One of the two internal standards is the normal ambient environment inside the instrument. Since the ambient air contains only a very small amount of $CO_2$ gas (typically 200 ppm) the ambient environment inside the instrument is treated in a de facto manner as a zero $CO_2$ standard. Care must of course be taken not to generate any $CO_2$ gas inside the instrument during the initial calibration of the instrument. The other internal standard takes the form of a hermetically sealed standard cell with transparent windows containing an appropriate amount of $CO_2$ gas; for example, 55 mmHg, to simulate an equivalence of 55 mmHg of $pCO_2$ flowing through the sample chamber of the instrument.

The unique optical system design affords the creation of eight specific measurements resulting in four ratios, sequentially in time and continuously. One of these measurement ratios is used to make the basic carbon dioxide measurement using the double-Q negative filtering technique as currently employed, for example, in commercially available $CO_2$ analyzers. The other three measurement ratios are employed to track and detect environmental and system component changes including the build-up of carbon dioxide gas inside the instrument and the possible leak of gas from the internal gas standard (55 mmHg). Environmental and system component changes detected by these three measurement conditions, or ratios, are used by the special calibration formalism or methodology mentioned to generate corrections in real time and applied to the carbon dioxide measurement via the use of microcomputer and associated electronic circuitry. It is in this manner than the continuously self-calibrating feature of the present invention is achieved. At the same time the need for a separate zero gas standard as used in present commercial instruments is eliminated. Furthermore, the need to standardize the exact $pCO_2$ value for the standard cells for different instruments is rendered unnecessary. The current invention further provides an automatic check for gas leaks in the standard cell not previously available in prior arts such as the Hewlett-Packard $CO_2$ analyzer.

DESCRIPTION OF THE DRAWINGS

FIG. 2 is a schematic diagram of the optical-mechanical apparatus embodying the invention and in which FIG. 2A is an enlargement of box 2 of FIG. 1; FIG. 2B is a plan view of the left-hand chopper wheel of FIG. 2A; and FIG. 2C is a plan view of the right-hand chopper wheel of FIG. 2A;

FIG. 3 is a table showing the correlation between the quadrants of the two wheels of FIGS. 2B and 2C and the sample chamber, and naming the voltage response of each combination;

FIG. 4A is a diagram of the wheels when they are aligned to pass radiant energy through the vacuum cell, open hole, and sample cell.

FIG. 4B is a diagram of the wheels when they are aligned to pass radiant energy through the reference cell, the open hole, and sample cell.

FIG. 5A is a diagram of the wheels when they are aligned to pass radiant energy through the vacuum cell and standard cell.

FIG. 5B is a diagram of the wheels when they are aligned to pass radiant energy through the reference cell and standard cell.

FIG. 6A is a diagram of the wheels when they are aligned to pass radiant energy through the vacuum cell and open hole.

FIG. 6B is a diagram of the wheels when they are aligned to pass radiant energy through the reference cell and open hole.

FIG. 7A is a diagram of the wheels when they are aligned to pass radiant energy through the vacuum cell, standard cell, and sample cell.

FIG. 7B is a diagram of the wheels when they are aligned to pass radiant energy through the reference cell, standard cell, and sample cell.

FIG. 8A is a diagram of the detector output voltage due to radiant energy passing through the various combinations of vacuum cell, reference cell, open hole, and standard cell of FIGS. 4A, 4B, 5A, 5B, 6A, 6B, 7A, and 7B, respectively.

FIG. 8B is a diagram of the sync detector output, with the double pulse indicating the beginning of the sequence of the various combinations, as shown in FIG. 3.

FIG. 8C is a diagram of the markings on the periphery of either one of the two wheels for the sync detector to generate the outputs shown in FIG. 8A.

FIG. 8D is a diagram of the signals for indicating the time to start the sampling of the detector outputs.

FIG. 8E is a diagram wherein the cross-hatched columns represent the time during which the detector outputs are sampled.

FIG. 8F is a diagram of the voltage levels of the detector outputs.

FIG. 8G is a diagram showing the correlation of the markings on the periphery of the wheel (FIG. 8C) with the various measurement numbers in the lefthand column of FIG. 3.

FIGS. 9A through 9K are schematics and a chart showing prior art: FIG. 9A showing radiant energy passing through a vacuum cell and a sample chamber; FIG. 9B showing radiant energy passing through a reference cell and the sample chamber; FIG. 9C showing radiant energy passing through a hole and the sample chamber.

FIG. 9D is a graph (1) of the outputs of FIGS. 9A and 9B and the Q-curve for the ratio of the $V_R$ and $V_S$ curves ($Q = V_R/V_S$); (2) a graph of the outputs of FIGS. 9B and 9C and the U-curve for the ratio of $V_R$ and $V_H$ curves ($U = V_R/V_H$); and (3) a graph of the outputs of FIGS. 9B and 9C and the U'-curve for the ratio of $V_R$ and $V_{H'}$ curves ($U' = V_R/V_{H'}$). Note that the difference between the outputs $V_H$ and $V_{H'}$ from FIG. 9C is that in the case of $V_H$ there is zero or negligible $CO_2$ present in spaces from S to D whereas for the case of $V_{H'}$ there is significant amount of $CO_2$ (greater than 2 mmHg) present in spaces from S to D in FIG. 9C.

FIGS. 9E, 9F and 9G are identical to FIGS. 9A, 9B and 9C respectively, with the exception that the sample chamber is replaced by a zero $CO_2$ standard (typically a sapphire blank). Similarly FIGS. 9H, 9J and 9K are identical to FIGS. 9A, 9B and 9C, respectively, with the exception that the sample chamber is replaced by a "span" $CO_2$ standard cell equivalent to 55 mmHg of $CO_2$ gas concentration. These arrangements are used to check the values for the calibration constants $Q_0$ and $Q_1$ in the Double-Q method as practiced in the current Hewlett-Packard Capnometer.

DETAILED DESCRIPTION OF THE INVENTION

Figure 1:
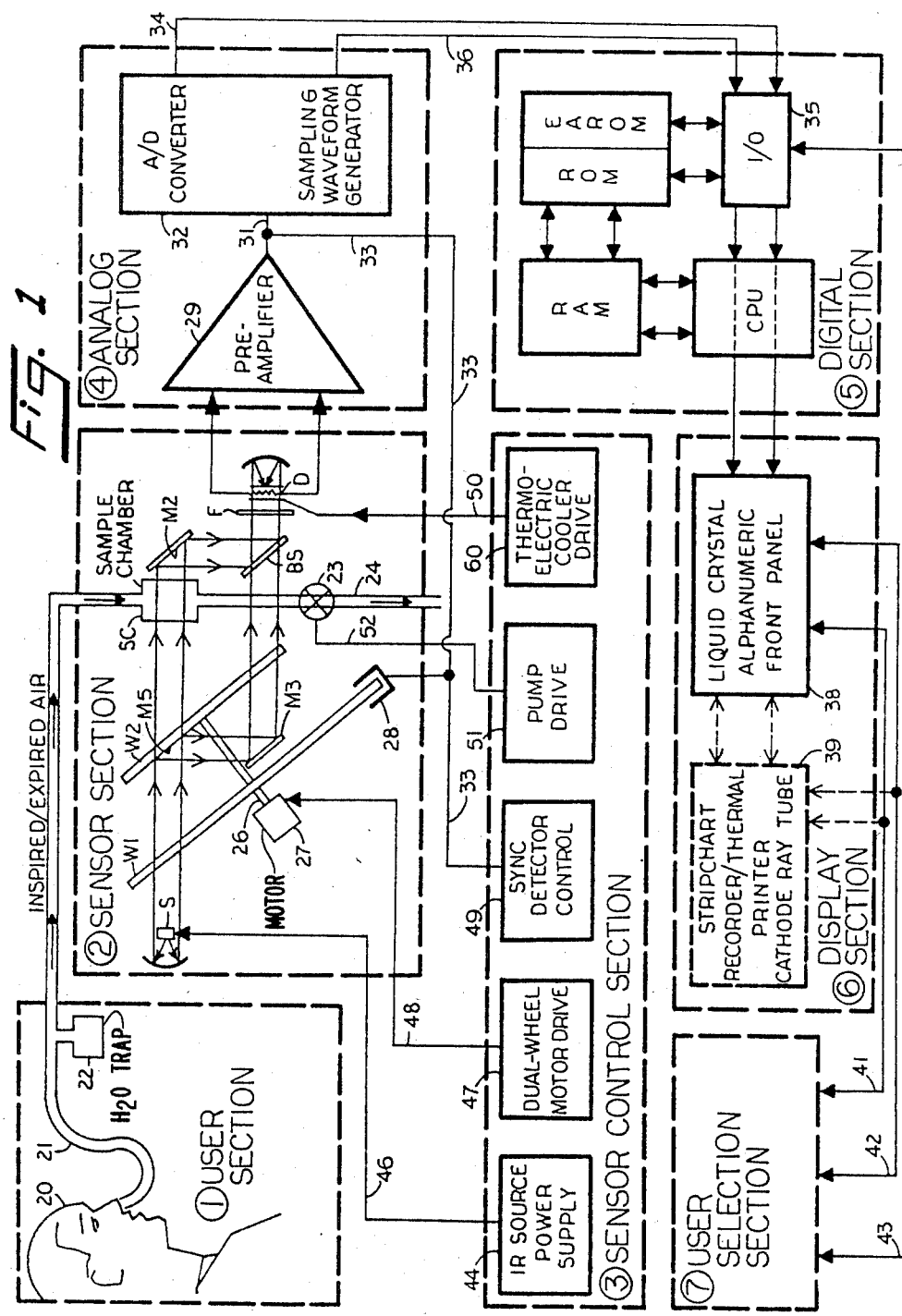
FIG. 1 is a block diagram of apparatus embodying the invention.
Figure 9A:
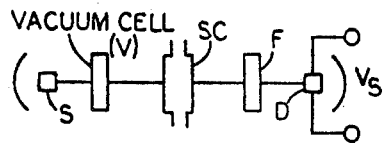
Figure 9B:
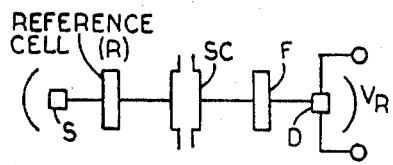
Figure 9C:
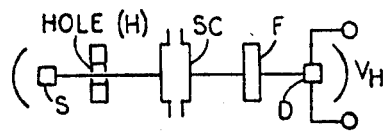
Figure 9D:
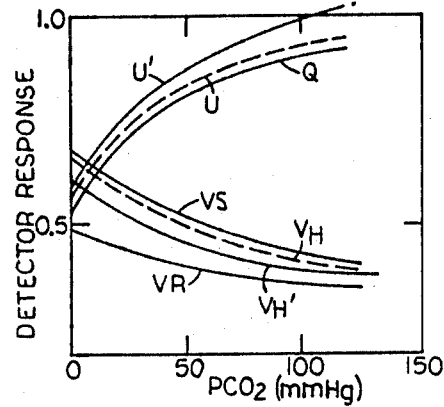
Figure 9E:
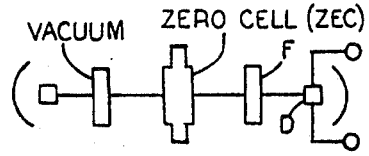
Figure 9F:
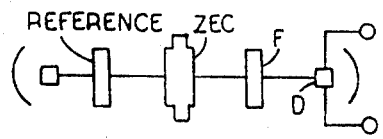
Figure 9G:
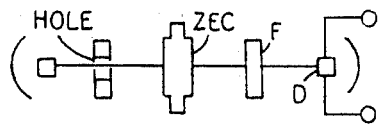
Figure 9H:
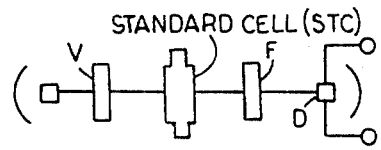
Figure 9J:
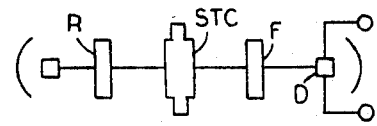
Figure 9K:
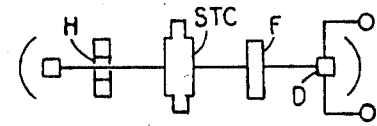

Referring to FIG. 1, block diagram or box 1 illustrates a patient 20 who is being monitored to measure the $CO_2$ content of the exhaled breath. A tube 21 is taped or otherwise secured in the vicinity of the patient's nose. The tube leads to a water trap 22 to remove the mucous content and the other end of the tube 21 is connected to box 2, the sensor section. This connection is brought to a transparent sample chamber SC through which the inhaled and exhaled breath passes, and a flow of inhaled and exhaled air is maintained by a pump 23 to which a tube 24 is connected to exhaust the air to the exterior of the apparatus.

The apparatus of box or section 2 is provided particularly in accordance with the invention and has as its novel elements dual chopper wheels W1 and W2 rotating in unison, which may be accomplished in several ways including a common shaft 26 rotated by a motor 27. The wheels are described with reference to FIG. 2 in more detail. In one part of a single rotation, radiation passes from a source S through transparent areas in the wheels W1 and W2 and through the transparent sample chamber SC to impinge upon a mirror M2 which can direct the radiation to a detector D directly, or indirectly by means of a semi mirror or beam splitter BS after traversing filter F.

As the wheels W1 and W2 rotate to a different position in a single rotation a mirror M5 on wheel W2 intercepts the radiation and directs it downwardly to a mirror M3 and from there the radiation passes through a transparent section in the bottom of wheel W2 as shown in FIG. 1, through the beam splitter BS, and through a filter F to the detector D. The filter is preferably of the interference type and passes only the desired radiation, which for $CO_2$ is preferably in the infrared part of the electromagnetic spectrum at about 4.26 microns.

The speed of the rotation of the chopper wheels W1 and W2 is matched to the characteristics and capabilities of the electronic circuits employed and I presently prefer about 3,000 rpm. The electrical output of detector D must be synchronized with the mechanical rotation of the wheels W1 and W2 and this is accomplished by magnetizing parts of one of the wheels, or otherwise sensitizing parts and a sync detector 28 is energized by these portions of wheel W1 to activate the electronic circuits at the precise intervals.

Considering now box or block 4 of FIG. 1, the analog section, the output of the detector D of block 2 is delivered to an amplifier 29 and the output is delivered by a conductor 31 to an analogue to digital converter 32. The conductor 31 is also connected by a wire 33 to the sync detector 28 so that the down stream circuits will be energized at the correct instants to correspond with the angular positions of wheels W1 and W2 during a single rotation. The analog section also contains circuits which sample the waveforms generated by the detector D for the various angular positions of the wheels W1 and W2 during a single rotation.

Referring still to FIG. 1, the output from the analog section 4 is fed by conductors 34 and 36 to an input-output logic circuit 35 more particularly described as an input logic and logic to output circuit. This is connected to a central processor unit or micro processor CPU located in box or block 5, the digital section. The input-output circuit 35 (I/O) is also connected to electrically alterable read-only-memory EAROM, a permanent program read-only-memory ROM, and a volatile random-access-memory RAM. The computation takes place in this digital section 5 and takes place at every revolution of the chopper wheels W1 and W2. The computation is performed to detect changes in the standard $CO_2$ cell as well as changes of $CO_2$ content inside the sensor of block diagram 2. The electrical waveforms received by the analog to digital converter are converted to digital form so that the computation and comparison can take place in the digital section 5.

The output of the digital section 5 of FIG. 1 may be converted to any desired form for reading and recording and for illustrative purposes section 6, display, may have a liquid crystal alphanumeric display 38, a strip chart recorder instrument, printer of any desired type or a cathode ray tube all designated by the block 39.

The selection of the type of display desired is made by the operator and is designated by the block or box 7. Leading from box 7 are conductors 41 and 42 connected to box 6 for selecting the type of display or recording as well as a conductor 43 leading to the input logic and logic to output circuit I/O of box 5.

Also included in FIG. 1 is a sensor control section 3, having a power supply 44 connected by conductor 46 to the radiation source S of box 2; having a power supply 47 connected by a conductor 48 to the motor 27 for obtaining extremely uniform speeds of rotation; having a sync detector control 49 connected to conductor 33; having a pump drive power supply 51 connected by conductor 52 to the pump 23; and having a cooler power supply 60 connected by conductor 50 to the detector D. The PbSe type of detector D which I presently prefer requires cooling and, while this can be done by a refrigerant gas or liquid, I prefer to do it electrically by using a thermoelectric cooler.

The operation of the apparatus of FIG. 1 is as follows: The electrical supplies of box 3, sensor control section, are manually turned on causing the apparatus of box 2 sensor section, to operate. The source S emits radiation which travels through openings in chopper wheels W1 and W2, through the sample chamber SC to the mirror M2 where it is reflected to beam splitter BS which directs it to the detector D after traversing filter F. The motor 27 rotates the wheels and the sync detector 28 passes signals on conductor 33 to the analog to digital converter 32 of box 4 to energize the electronics at the precise instants that the chopper wheels pass radiation. At one part of the rotation of W1 and W2, mirror M5 on W2 will direct radiation to mirror M3, which directs it through the beam splitter BS to the detector D after traversing filter F. During operation the pump 23 draws air from the patient 20 through hose 21 to the sample chamber SC, where its $CO_2$ content absorbs radiation and this absorption is detected by D. Filter F limits the spectrum to the desired frequency; for example, 4.26 microns for measuring $CO_2$.

The output of detector D is amplified at 29 and is in the form of analog pulses which are converted to digital form and directed in synchronism with the mechanical rotation of wheels W1 and W2 to the digital section 5, where measurements are compared to standards and stored, compared to changing values, and calculations are made by the central processor unit CPU to detect changes in $CO_2$ gas within the sensor section 2 and any changes in the gas concentration in the $CO_2$ standard.

The user selects the type of readout and/or recording he desires by operating controls at box 7, which can cause alphanumeric readout at 38 or a cathode ray tube at 39 or can record by stripchart or computer printout at 39.

FIG. 2

Illustrated in FIG. 2A is most of the apparatus of box or block 2 of FIG. 1, the sensor section. Instead of a single shaft for the chopper wheels W1 and W2, there is disclosed two shafts 46 and 47 driven by a single spur gear 48 to give synchronized rotation of the two chopper wheels. The shafts 46 and 47 may be at 45° to a first optical path 49, but it will be appreciated that both wheels W1 and W2 could be mounted on a single shaft that is parallel to the first optical path 49, and in this case the mirror M5 will be at an angle on its wheel to deliver radiation to mirror M3. The mirror M3 and detector D define a second optical path 51.

Referring now to FIG. 2B, wheel W1 has eight openings numbered 1 through 8. Openings 6,7,8 and 1 are occupied by a transparent vacuum cell 52 which is an envelope preferably of the same axial thickness as the wheel W1. The envelope is evacuated, or may be filled with a gas that contains no $CO_2$ and does not absorb radiant energy of the wave band being utilized. Openings 2,3,4 and 5 of wheel W1 are occupied by a transparent reference cell 53 containing a high concentration of the gas being analyzed, for example 380 mmHg of $CO_2$. Reference cell 53 is also preferably of the same axial thickness of wheel W1 and this high concentration will absorb a large percentage of the radiation as shown by curve $V_R$ on FIG. D. $V_R$ refers to the voltage at detector D when radiation passes through the "reference" cell 53.

Referring now to FIG. 2C, wheel W2 also has eight openings numbered 1 through 8 in the same relative positions of openings 1 through 8 of wheel W1 (FIG. 2B). Openings 8,1,2 and 3 are occupied by the mirror M5. Openings 4 and 7 are clear and unobstructed holes 55 through the wheel W2. Openings 5 and 6 are occupied by a transparent standard cell or span cell 54, which is an envelope having $CO_2$ of a known partial pressure and I presently prefer 55 mmHg or 55 torrs of $CO_2$. Preferably also, the standard cell 54 has the same axial width as the wheel W2.

OPERATION OF FIG. 2

The wheels W1 and W2 rotate in unison and the opening 1 of wheel W1 will be aligned with opening 1 of wheel W2 in the first optical path 49. Successively, the opening pairs 2—2, 3—3, 4—4, 5—5, 6—6, 7—7 and 8—8 will be aligned when they are disposed in the first path 49. The spaces between the wheel openings are opaque, and thus each rotation chops up the radiation from source S into discrete pulses of radiation, and for this reason the wheels W1 and W2 are designated as "chopper wheels". The detector D therefore receives intermittent radiation from the source S.

Referring particularly to FIG. 2A when openings 8,1,2 and 3 of wheel W2 are disposed in the first path 49 the mirror M5 directs radiation along a path 56 to the mirror M3. At any of these interceptions by mirror M5, the diametrically opposite openings 4,5,6 and 7 of W2 will transmit radiation because they are either a hole 4 or 7 or are occupied by the transparent standard cell 54. Therefore, whenever the mirror M5 prevents radiation from reaching the sample cell SC and the mirror M2, the second path 51 is receiving radiation. All openings of wheel W1 transmit radiation.

FIG. 2A therefore shows two distinct radiation paths that occur during a single rotation of the wheels W1 and W2. One path is from source S through openings 4,5,6 and 7 of wheel W1, through openings 4,5,6 and 7 of wheel W2, through the sample chamber SC to the mirror M2, to the beam splitter (semi mirror) BS, through the filter F to the detector D. The other path is from source S through openings 8,1,2 and 3 of wheel W1, to the mirror M5 of wheel W2 openings 8,1,2 and 3, to the mirror M3, through openings 4, 5, 6 and 7 in wheel W2, through the beam splitter BS, and through the filter F to the detector D.

FIGS. 4, 5, 6 and 7

The radiation reaching the eight openings of each wheel W1 and W2 are arranged in four pairs to give four separate ratios of $V_R$ over $V_S$, meaning that in each pair of measurements one measurement is made by radiation passing through the reference cell 53 and the other measurement is from radiation passing through the vacuum cell 52, each in combinations with the sample chamber SC, open holes 4 and 7 of W2 and the standard cell 54 of W2.

FIG. 4A shows the combination of radiation vacuum cell 52, open hole and sample chamber. FIG. 4B shows the combination of reference cell 53, open hole and sample chamber. In FIG. 4 the sample chamber SC is in the radiation path.

FIG. 5A shows the combination of vacuum cell 52 and standard cell 54. FIG. 5B shows the combination of reference cell 53 and standard cell. In FIG. 5, the standard cell is substituted for the sample chamber which is out of the radiation path.

FIG. 6A shows the combination of vacuum cell 52 and open hole 55 of W2. FIG. 6B shows the combination of reference cell 53 and open hole 55 in W2. In FIG. 6 the sample chamber is out of the radiation path.

FIG. 7A shows the combination of vacuum cell 52, standard cell 54 and sample chamber SC. FIG. 7B shows the combination of reference cell 53, standard cell 54 and sample chamber SC. In FIG. 7 the sample chamber SC is in the radiation path.

FIG. 3

These paths of FIGS. 4, 5, 6 and 7 are tabulated in FIG. 3, which also numbers in the left-hand column the eight measurements. In the next column there is stated the function that each pair of measurements performs. In the columns headed W1 and W2 there are stated the opening numbers of W1 and W2. The "sample cell" column states whether or not the sample cell is in the radiation path, or out of the radiation path. The "measurement" column gives the voltage symbols for each of the eight measurements.

Measurements numbers 1 and 2 are performed automatically in the prior art and measurements 3 and 4 are performed manually in the prior art. Measurements 5, 6, 7 and 8 are applicant's novel contribution to the art that enable the instrument to be self correcting or self-calibrating and which also detect any leakage of the standard cell 54.

FIG. 8

Illustrated in FIG. 8 is the sampling of the output of detector D of FIG. 1 (also FIGS. 2, 4-7). The full sequence of measurement numbers of the left-hand column of FIG. 3 is repeated in the horizontal line FIG. 8C and there it will be noted that measurement numbers 1, 2 and 3 of the following or next rotation also appear for fuller illustration.

Illustrated in FIG. 8A are representative output voltages from the detector D. Measurement 1 is a higher wave form than measurement 2 because the vacuum cell (FIG. 3) of measurement 1 absorbs less of the radiation than the reference cell of measurement 2. The relative heights of the other output voltages are also explained with reference to FIG. 3.

FIG. 8G illustrates the synchronizing material disposed in different sectors of periphery wheel W1 so that the position of the two wheels at any instant may be sensed by sync detector 28 of FIG. 1 (box 2). Sector 1 of W1 has a split synchronized (or magnetic) material 56 so that it can be identified, whereas sector 3 has material 57 for the full sector, and sectors 5 and 7 also have full material 57. The output of sync detector 28 is illustrated in the square wave forms of FIG. 8B and the output signal from detector 28 is shown by the cross hatching in FIG. 8C.

The sync detector control 49 of FIG. 1 generates a pulse for each sector as it rotates into the radiation first path 49 (FIG. 2). These are sampling pulses and are shown in FIG. 8D. These sampling pulses cause the sampling of the wave form of FIG. 8A which results in samples close to the peak of the wave forms of FIG. 8A. The samples are shown in crosshatch in FIG. 8E. The heights or strength of each sample is shown in FIG. 8F. It is these analog heights of FIG. 8F that are converted to digital form by the analog to digital converter 32 of FIG. 1. These digital values are fed into the storage and computing section or box 5 of FIG. 1.

RECALIBRATION TECHNIQUE USED IN THE PRESENT INVENTION

Following the double-Q negative filtering technique employed in prior art the $pCO_2$ in the sample chamber can be represented by a calibration S-curve in the form:

$$pCO_2(mmHg) = A_0 + A_1 S + A_2 S^2$$

where S is defined as $$S = \frac{Q - Q_0}{Q_1 - Q_0}$$

and $$Q = \frac{V_R}{V_S}$$

where $V_R$, $V_S$ are the transduced voltages, numbers 1 and 2 of FIG. 3, at the detector D for the "reference" and "sample" beam, respectively, as described in the Negative Filtering Method. $Q_0$ is given by $$Q_0 \equiv \frac{V_R}{V_S}\bigg|_{0 \text{ mmHg}}$$

when there is zero $CO_2$ flowing through the sample chamber and $Q_1$ is given by $$Q_1 \equiv \frac{V_R}{V_S}\bigg|_{55 \text{ mmHg}}$$

when there is $CO_2$ of 55 mmHg concentration flowing through the sample chamber.

The quantities $A_0$, $A_1$ and $A_2$ are coefficient constants empirically determined based upon the experimental calibration curve of the instrument.

THREE ADDITIONAL MEASUREMENT RATIOS

I now define three more Q's as follows:

$$Q_S = V_R'/V_S'$$

as shown in FIG. 5 when the sample chamber is out of the energy path and the standard cell is in the energy path (hence $Q_S$), and $$Q_A = V_R''/V_S''$$

as shown in FIG. 6 when there is ambient or negligible (hence $Q_A$) $CO_2$ inside of the instrument enclosure and the sample chamber is out of the energy path, and $$Q_I = V_S^0/V_R^0$$

as shown in FIG. 7 wherein the standard cell and the sample chamber are in series.

As described with reference to FIGS. 1-7, the unique dual-wheel optical system design for the present invention sets up these three measurement ratios or conditions, in addition to that used to measure $CO_2$ via $$Q = V_R/V_S.$$

One such measurement is shown in FIG. 5 and gives the ratio $$Q_S = V_R'/V_S'.$$

In this case, an optical arrangement is set up in such a way that the sample chamber SC is temporarily by-passed. In its place is the "span" or standard cell. Again, a "reference" and a "samle" beam is set up to yield transduced voltages of $V_R'$ and $V_S'$ respectively. $Q_S$ is simply defined as the ratio $$V_R'/V_S'.$$

This arrangement in essence measures an effective $CO_2$ gas standard represented by the $pCO_2$ content in the sealed standard cell. In practice, this $CO_2$ gas standard can be set approximately at 55 mmHg of $CO_2$ gas by adjusting the amount of $CO_2$ inside the sealed cell during filling. Verification can easily be made with the help of the original calibration S-curve by substituting $S_S$ for S to obtain $$pCO_2(\text{mmHg}) = A_0 + A_1 S_S + A_2 S_S^2$$

where $$S_S = (Q_S - Q_0)/(Q_1 - Q_0)$$

and $Q_0$ and $Q_1$ are defined earlier.

Another such measurement condition is illustrated in FIG. 6 and gives the ratio $$Q_A = V_R''/V_S''.$$

In those wheel positions, an optical arrangement is set up such that the sample chamber is temporarily by-passed. In its place is a volume of the ambient environment inside the instrument represented by an open hole in the dual-wheel assembly. Like the basic measurement for $CO_2$, a "reference" and a "sample" beam is set up (measurement numbers 5 and 6, FIG. 3). The transduced voltages at the detector are called $V_R''$ and $V_S''$ respectively, and $$Q_A = V_R''/V_S''.$$

This particular measurement, in essence, monitors the $CO_2$ level inside the instrument. The measured $Q_A$ can be used to deduce indirectly the $CO_2$ concentration inside the instrument by using the calibration S-curve $pCO_2(\text{mmHg}) = A_0 + A_1 S_A + A_2 S_A^2$, where $S_A$, in this case, is given by $$S_A = (Q_A - Q_0)/(Q_1 - Q_0)$$

The third measurement condition is shown in FIG. 7 and gives the ratio $$Q_I = V_R^0/V_S^0.$$

In this case, an optical arrangement is set up in such a way that the standard cell and the sample chamber SC line up in series with each other. Both the "reference" beam and the "sample" beam traverse this series combination of standard cell and sample chamber, and the transduced voltages so obtained at the detector are designated as $V_R^0$ and $V_S^0$ respectively. The ratio $Q_I$ is defined as the ratio $V_R^0/V_S^0$ as before. This optical arrangement, in effect, measures the sum of the $CO_2$ level in both the standard cell and the sample chamber. I have discovered that the values of Q and $Q_I$ are related in a predictable way. I utilize this discovery in the current invention to continuously monitor any leakage that might occur in the standard cell.

UTILIZING THE QS FOR SELF-CALIBRATION

I utilize the simultaneous measurements for the values of Q, $Q_S$, $Q_A$, and $Q_I$ during each dual-wheel revolution for the desirable result of continuous self-calibration for the current invention for a $CO_2$ analyzer. Whereas the double-Q negative filtering technique needs to establish initially two Q values, namely, $Q_0$ and $Q_1$, the current invention needs to establish two more Q values initially, namely, $Q_A^o$ and $Q_S^o$. $Q_A^o$ is defined as the value of $Q_A$ when care is deliberately taken to insure that the $CO_2$ concentration inside the instrument is no higher than the ambient $CO_2$ level, or typically 200 ppm. $Q_S^o$ is defined as the value of $Q_S$ under the same condition when $Q_A^o$ is determined. Like $Q_0$ and $Q_1$ both $Q_A^o$ and $Q_S^o$ are determined experimentally in the beginning and stored away in EAROM in the computer section 5 of FIG. 1 of the $CO_2$ instrument.

The value of Q is used along with $Q_0$ and $Q_1$ to make the basic $CO_2$ measurement following the double-Q method. The values of $Q_S$ and $Q_A$ are used to monitor the changes in $Q_S^o$ and $Q_A^o$ in time after their initial determination. The value of $Q_I$ is used to monitor any leakage in the span standard cell.

It is important to note that $Q_A^o \approx Q_0$ and $Q_S^o \approx Q_1$. This substantial equality can be effected by tailoring, in the case of $Q_A^o$, the optical aperture of the open hole in the dual-wheel assembly and in the case of $Q_S^o$ the amount of $CO_2$ present in the standard cell.

In practice, this equality must be verified by using the original calibration S-curve of the instrument. Since the dual-wheel assembly and the span standard cell are unique to each individual instrument, and hence to the accompanying calibration S-curve, this established equality between $Q_A^o$ and $Q_0$ and $Q_S^o$ and $Q_1$ are self-consistent.

By virtue of the fact that $Q_A^o \approx Q_0$ and $Q_S^o \approx Q_1$ the application of detected changes in $Q_A$ and $Q_S$, namely, $\Delta Q_A = Q_A - Q_A^o$ and $\Delta Q_S = Q_S - Q_S^o$, directly to $Q_0$ and $Q_1$ is equivalent to the double-Q recalibration method currently practiced in the Hewlett-Packard $CO_2$ analyzer. However, since $Q_A$ and $Q_S$ are being continuously monitored for environmental and/or component changes that could possible alter their values, any detected changes in $Q_A$ and $Q_S$ can be applied immediately to $Q_0$ and $Q_1$ for restoring the instrument accuracy, thus rendering it continuously self-calibrating.

It can be shown with a little algebra that in the event $Q_A^o$ and $Q_S^o$ are not exactly equal to $Q_0$ and $Q_1$, respectively, then the corrections to be applied to $Q_0$ and $Q_1$ for detected changes in $Q_A$ and $Q_S$, namely, $\Delta Q_A$ and $\Delta Q_S$ where $$\Delta Q_A = Q_A - Q_A^o$$

$$\Delta Q_S = Q_S - Q_S^o$$

are given by $$\Delta Q_0 = \left(\frac{K_1}{K_1 - K_2}\right) \Delta Q_S - \left(\frac{K_2}{K_1 - K_2}\right) \Delta Q_A \quad (1)$$

$$\Delta Q_1 = \left(\frac{K_1 - 1}{K_1 - K_2}\right) \Delta Q_S - \left(\frac{K_2 - 1}{K_1 - K_2}\right) \Delta Q_A \quad (2)$$

where $$K_1 = \frac{-A_1 + \sqrt{A_1^2 - 4A_2(A_0 - P_A)}}{2A_2}$$

$$K_2 = \frac{-A_1 + \sqrt{A_1^2 - 4A_2(A_0 - P_S)}}{2A_2}$$

and $P_A$ and $P_S$ are the $pCO_2$ values corresponding to $Q_A^o$ and $Q_S^o$ (or $S_A^o = (Q_A^o - Q_0)/(Q_1 - Q_0)$ and $S_S^o = (Q_S^o - Q_0)/(Q_1 - Q_0)$) according to the original calibration S-curve of the instrument, viz.

$$pCO_2(\text{mmHg}) = A_0 + A_1 S + A_2 S^2$$

or $$P_A = A_0 + A_1 S_A^o + A_2 (S_A^o)^2$$

and $$P_S = A_0 + A_1 S_S^o + A_2 (S_S^o)^2$$

It is worth noting that when $P_A = 0$, then $K_1 = 0$, and when $P_S = 55$ mmHg, then $K_2 = 1$. In this case, Eqs. 1 and 2 reduce respectively to $\Delta Q_0 = \Delta Q_A$ and $\Delta Q_1 = \Delta Q_S$, as required.

CHECKING THE STANDARD CELL

I have discovered that a simultaneous measurement of Q and $Q_I$ enables the span or standard cell to be continuously checked for leakage. The proof of this discovery is as follows. At any instant of time, the measurement of Q hence, $$S = (Q - Q_0)/(Q_1 - Q_0)$$

gives the $CO_2$ level present in the sample chamber SC. Similarly, the measurement of $Q_I$ hence, $$S_I = (Q_I - Q_0)/(Q_1 - Q_0)$$

gives, in effect, the sum of $CO_2$ present in the standard cell (55 mmHg) and in the sample chamber. Using the calibration curve for the instrument, we have $$P = A_0 + A_1 S + A_2 S^2 \quad (3)$$

where P is the $CO_2$ level in the sample chamber. Also, we have $$P_S = A_0 + A_1 S_S + A_2 S_S^2 \quad (4)$$

where $P_S$ is the effective $pCO_2$ in the standard cell and $$S_S = (Q_S^o - Q_0)/(Q_1 - Q_0)$$

is the corresponding quantity obtained from $Q_S^o$. Note that $Q_S^o$ (and, hence, $S_S$) is stored as a calibration constant and is retrievable from the computer memory on demand. Furthermore, $$P + P_S = Q_0 + A_1 S_I + A_2 S_I^2 \quad (5)$$

where $$S_I = (Q_I - Q_0)/(Q_1 - Q_0)$$

Thus, by adding Equations (3) and (4), and comparing the sum with Equation (5), one has $$A_2 S_I^2 + A_1 S_I + C = 0 \quad (6)$$

where $C = -[A_0 + A_1(S + S_S) + A_2(S^2 + S_S^2)]$

Equation (6) can be solved to yield $$S_I = \frac{-A_1 + \sqrt{A_1^2 - 4A_2 C}}{2A_2} \quad (7)$$

$$= \frac{-A_1 + \sqrt{A_1^2 + 4A_2[A_0 + A_1(S + S_S) + A_2(S^2 + S_S^2)]}}{2A_2}$$

In equation (7), everything is known ($A_0$, $A_1$, $A_2$, are stored in non-volatile ROM and S and $S_S$ are calculated from the measured values of Q and the stored value of $Q_S^o$ (in EAROM), respectively.

Thus, by checking the self-consistency of Equation (7) above, namely by comparing the calculated value for $S_I$ using Equation (7) with $S_I$ actually being measured (FIG. 7), one can readily deduce whether $S_S$ stays constant as it should be. The calculated value for $S_I$ should agree with that being measured if there is no leak in the span standard cell. In this fashion, there is a continuous check of the standard cell for leakage, which is important because the S-curve calibration is based upon the gas content of the standard cell.

$CO_2$ CALCULATION AND SELF-CALIBRATION USING THE COMPUTER

The digital electronics (FIG. 1, box 5) needed to generate the $CO_2$ output value and to accomplish the continuously self-calibrating function of the current invention for a $CO_2$ analyzer consists of a microprocessor, volatile random-access-memory (RAM), permanent program read-only-memory (ROM), a non-volatile but electrically alterable ROM (EAROM), and input logic and logic to output information to the user 35 (I/O).

The original calibration S-curve for the instrument is permanently stored in ROM in the form of three coefficient constants $A_0$, $A_1$, and $A_2$. These coefficient constants are experimentally and a priorily determined according to procedures that are well-known to those knowledgeable in the art of $CO_2$ gas analyzers. Four additional parameters, $Q_0$, $Q_1$, $Q_S^o$, and $Q_A^o$, which are similarly determined, are stored in EAROM.

If either $Q_A^o \neq Q_0$ or $Q_S^o \neq Q_1$, then two additional initial parameters $K_1$ and $K_2$ (see section under "Utilizing the Qs for Self-Calibration") are also stored in ROM. The values of $K_1$ and $K_2$ depend upon the values of $Q_A^o$ and $Q_S^o$ and the original calibration S-curve for the instrument as explained in the section cited. The manner by which they are determined is also well-known to those knowledgeable in the business of manufacturing $CO_2$ gas analyzers.

In addition, three constants, $\Delta I$, $\Delta A$, and $\Delta S$, are stored in ROM. The value of $\Delta I$ is used to determine whether the span standard cell is leaktight. The values of $\Delta A$ and $\Delta s$ are used to determine if the characteristics for the components inside the instrument have changed to the extent, due either to aging or external stimuli, that a recalibration is needed to restore the performance accuracy of the instrument.

Under normal operation a new set of Q values, namely, Q, $Q_A$, $Q_S$, and $Q_I$ are fed, during each dual-wheel revolution, into the Central Processing Unit (CPU) of the microprocessor via the input logic 35 for data processing.

CHECKING FOR LEAKAGE IN SPAN STANDARD CELL

Using the input values of Q and $Q_I$ and retrieving the values of $Q_S^o$, $Q_0$ and $Q_1$ stored in EAROM, the CPU computes the values for S, $S_S$, and $S_I$ according to the relations already cited, viz.

$$S = (Q - Q_0)/(Q_1 - Q_0)$$

$$S_S = (Q_S^o - Q_0)/(Q_1 - Q_0)$$

and $$S_I = (Q_I - Q_0)/(Q_1 - Q_0)$$

Using the values of S and $S_S$ just computed and further retrieving the values of $A_0$, $A_1$, and $A_2$ from ROM, the CPU calculates a value $S_I^*$, which is the expected value for $S_I$ if the span standard cell is leaktight according to the formula:

$$S_I^* = \frac{-A_1 + \sqrt{A_1^2 + 4A_2[A_0 + A_1(S + S_S) + A_2(S^2 + S_S^2)]}}{2A_2}$$

The CPU next calculates the absolute value of $S_I - S_I^*$, namely, $|S_I - S_I^*|$, and checks whether this value exceeds $\Delta I$, which is retrieved from ROM.

If $|S_I - S_I^*|$ exceeds $\Delta I$, then the span standard cell is leaking $CO_2$ gas. (Note that in actual practice this detected inequality must be allowed to repeat itself several times in succession before the microprocessor declares that the span standard cell is not leaktight.) In the event that the span standard cell is actually verified to be leaking $CO_2$ gas, an "inoperative" sign is instructed to be displayed on the display panel of the instrument (FIG. 1, box 6) via the output logic of the digital electronics (FIG. 1, box 5).

If $|S_I - S_I^*|$ is less than $\Delta I$, then the span standard cell is leaktight and the microprocessor proceeds to next programmed function.

CHECKING FOR SHIFTS IN $Q_A^o$ AND $Q_S^o$

Using the input values of $Q_A$ and $Q_S$ and retrieving the values of $Q_A^o$ and $Q_S^o$ from EAROM, the CPU computes $\Delta Q_A$ and $\Delta Q_S$ using the formulae:

$$\Delta Q_A = Q_A - Q_A^o$$

and $$\Delta Q_S \times Q_S - Q_S^o$$

Next the CPU checks the magnitudes for $\Delta Q_A$ and $\Delta Q_S$ by comparing respectively their absolute values with the values $\Delta A$ and $\Delta S$ stored in ROM. If either $|\Delta Q_A| > \Delta A$ or $|\Delta Q_S| > \Delta S$, then the instrument requires recalibration. Otherwise, the CPU is ready to calculate the $CO_2$ output values.

RECALIBRATION OR SELF-CALIBRATION

To do this, the CPU recalls the values for $K_1$ and $K_2$ from ROM and together with the values of $\Delta Q_A$ and $\Delta Q_S$ just calculated computes the values for $\Delta Q_0$ and $\Delta Q_1$ according to the formulae:

$$\Delta Q_0 = \left(\frac{K_1}{K_1 - K_2}\right) \Delta Q_S - \left(\frac{K_2}{K_1 - K_2}\right) \Delta Q_A$$

$$\Delta Q_1 = \left(\frac{K_1 - 1}{K_1 - K_2}\right) \Delta Q_S - \left(\frac{K_2 - 1}{K_1 - K_2}\right) \Delta Q_A$$

The calculated values of $\Delta Q_0$ and $\Delta Q_1$ are added or subtracted from the values of $Q_0$ and $Q_1$ retrieved from EAROM dependent upon the sign of $\Delta Q_0$ and $\Delta Q_1$ to form the new $Q_0$ and $Q_1$ values, viz.

$$Q_0^N = Q_0 + \Delta Q_0$$

$Q_1{}^N = Q_1 + \Delta Q_1$

The old set of $Q_0$, $Q_1$, $Q_A{}^o$, and $Q_S{}^o$ values are next erased from the EAROM, and a new set of Q values comprising $Q_0{}^N$, $Q_1{}^N$, $Q_A$, and $Q_S$ are now stored in their place in EAROM. Note that the previously stored values for $Q_A{}^o$ and $Q_S{}^o$ are being replaced by the most current $Q_A$ and $Q_S$ values, respectively.

CO₂ OUTPUT VALUE CALCULATION

The CPU next retrieves the most recent values of $Q_0$ and $Q_1$ (note that these values may have just been updated) from EAROM and together with the input value of Q calculates the parameter S according to:

$$S = (Q - Q_0)/(Q_1 - Q_0)$$

It then retrieves the values of $A_0$, $A_1$, and $A_2$ from ROM and calculates the CO₂ value according to:

$$pCO_2(mmHg) = A_0 + A_1 S + A_2 S^2$$

This will be the pCO₂ value outputted to the display panel for display via the output logic (FIG. 1, box 5). In the following claims the symbols used are defined as:
Q is $V_R/V_S$
$Q_0$ is $V_R/V_S$ when there is no CO₂ in the sample chamber (determined empirically)
$Q_1$ is $V_R/V_S$ when a known concentration of CO₂ is flowed through the sample chamber, such as 55 mmHg.
$Q_S$ is $V_R'/V_S'$ when sealed standard cell of known concentration is substituted for the sample chamber.
$Q_A$ is $V_R''/V_S''$ when an open hole in the chopper wheel is substituted for the standard cell and the sample chamber is out of the path.
$Q_A{}^o$ is the value of $Q_A$ when the CO₂ concentration inside the instrument is that of ambient air (empirically determined)
$Q_S{}^o$ is the value of $Q_S$ when the CO₂ concentration inside the instrument is that of ambient air (empirically determined)
$Q_I$ is $V_R{}^o/V_S{}^o$ when the standard cell and the sample cell are in series.
$S = (Q - Q_0)/(Q_1 - Q_0)$
$S_S = (Q_S - Q_0)/(Q_1 - Q_0)$
$S_A = (Q_A - Q_0)/(Q_1 - Q_0)$ and
$S_I = (Q_I - Q_0)/(Q_1 - Q_0)$
$A_0$, $A_1$ and $A_2$ are coefficients empirically determined to represent the calibration S-curve and are stored in ROM
S-curve is $pCO_2(mmHg) = A_0 + A_1 S + A_2 S^2$
$\Delta Q_A = Q_A - Q_A{}^o$
$\Delta Q_S = Q_S - Q_S{}^o$
ΔI stored, is the selected tolerance for standard cell leakage
ΔA stored, is the selected tolerance for CO₂ inside the instrument
ΔS stored, is the selected tolerance for other component changes affecting the standard cell pCO₂ value
$K_1$ is $$\frac{-A_1 + \sqrt{A_1{}^2 - 4A_2(A_0 - P_A)}}{2A_2}$$

$K_2$ is $$\frac{-A_1 + \sqrt{A_1{}^2 - 4A_2(A_0 - P_S)}}{2A_2}$$

$S_1{}^* =$ $$\frac{-A_1 + \sqrt{A_1{}^2 + 4A_2[A_0 + A_1(S + S_S) + A_2(S^2 + S_S{}^2)]}}{2A_2}$$

The following are the electrical changes of the detector when radiant energy passes through the following elements:
$V_S$: vacuum cell and open hole and sample cell,
$V_R$: reference cell and open hole and sample cell,
$V_S'$: vacuum cell and standard cell,
$V_R'$: reference cell and standard cell,
$V_S''$: vacuum cell and open hole,
$V_R''$: reference cell and open hole,
$V_S{}^o$: vacuum cell and open hole and sample cell,
$V_R{}^o$: reference cell and standard cell and sample cell.

I claim:

1. Optical-mechanical apparatus for a gas analyzer for generating electrical signals for continuously and automatically self-calibrating the electrical output comprising:
   (a) a first chopper wheel containing openings occupied by two items of (1) vacuum cell, (2) reference cell, (3) open hole, (4) standard cell;
   (b) a second chopper wheel containing openings occupied by the other two items of element "a" above;
   (c) means for aligning the openings of the two wheels to define a path;
   (d) means for rotating the two wheels in synchronism to align selected openings in the two wheels along said path;
   (e) a source of radiant energy disposed at one end of said path;
   (f) a sample chamber disposed along said path downstream from said wheels;
   (g) an electrical transducer detector of radiant energy disposed at the other end of said path to create changes in electrical quantities,
   whereby the detector creates values $V_S$, $V_R$, $V_S'$, $V_R'$, $V_S''$, $V_R''$, $V_S{}^o$, and $V_R{}^o$, for use in rendering the gas analyzer self-calibrating, and wherein these values are:
   $V_S$: vacuum cell and open hole and sample cell,
   $V_R$: reference cell and open hole and sample cell,
   $V_S'$: vacuum cell and standard cell,
   $V_R'$: reference cell and standard cell,
   $V_S''$: vacuum cell and open hole,
   $V_R''$: reference cell and open hole,
   $V_S{}^o$: vacuum cell and standard cell and sample cell,
   $V_R{}^o$: reference cell and standard cell and sample cell.

2. Apparatus as set forth in claim 1 wherein a filter is disposed in the path to pass only a selected portion of the electromagnetic spectrum.

3. Apparatus as set forth in claim 1 wherein the two wheels are mounted on the same axle.

4. Optical-mechanical apparatus for a gas analyzer for generating electrical signals for continuously self-calibrating the analyzer output comprising:
   (a) a source of radiant energy radiating energy along a first path;

(b) an electrical transducer detector for receiving energy at one end of a second radiant energy path;

(c) a first mirror disposed at the other end of said first path and directing energy on said detector;

(d) a second mirror disposed at the other end of said second radiant energy path;

(e) a first chopper wheel containing openings and rotatable to dispose selected openings in said first path, said openings occupied by two items of (1) vacuum cell, (2) reference cell, (3) open hole, (4) standard cell;

(f) a second chopper wheel containing openings occupied by the other two of said items of "e" above and also containing mirrors and rotatable to dispose selected openings on both paths, said chopper wheel mirrors being so disposed that energy in the first path is directed to the second mirror in the second path;

(g) a sample chamber disposed in said first path downstream from the chopper wheels; and (h) means for synchronizing the rotation of the two wheels to dispose selected openings simultaneously in the two paths;

whereby said detector generates electrical signals of $V_S$, $V_R$, $V_S'$, $V_R'$, $V_S''$, $V_R''$, $V_S^o$, and $V_R^o$, and wherein these signals result from radiant energy passing through the following wheel openings:

$V_S$: vacuum cell and open hole and sample cell,
$V_R$: reference cell and open hole and sample cell,
$V_S'$: vacuum cell and standard cell,
$V_R'$: reference cell and standard cell,
$V_S''$: vacuum cell and open hole,
$V_R''$: reference cell and open hole,
$V_S^o$: vacuum cell and standard cell and sample cell,
$V_R^o$: reference cell and standard cell and sample cell.

5. Apparatus as set forth in claim 4 wherein a beam splitter is disposed in the second path downstream from the second chopper wheel and the first mirror directs energy on the beam splitter to thereby direct energy from the first path to the detector.

6. Apparatus as set forth in claim 4 wherein a filter is disposed immediately upstream from the detector.

7. In a gas measurement apparatus employing sample chamber, a reference cell and a vacuum cell to obtain $V_R/V_S$ measurement, a standard cell for calibration and a computer, the method of detecting leakage in the standard cell comprising:

(a) storing in permanent memory at least three numerical coefficients $A_0$, $A_1$, and $A_2$ to represent the calibration S-curve;

(b) storing in nonvolatile but erasable memory $Q_0$, $Q_1$, and $Q_S^o$;

(c) continuously measuring $V_R$ when the reference cell and the sampling chamber are in series;

(d) continuously measuring $V_S$ when the vacuum cell and the sampling chamber are in series;

(e) continuously ratioing said $V_R$ over said $V_S$ to obtain $Q(Q=V_R/V_S)$;

(f) continuously measuring $V_R^o$ when the reference cell, standard cell, and sampling chamber are in series;

(g) continuously measuring $V_S^o$ when the vacuum cell, standard cell, and sampling chamber are in series;

(h) continuously ratioing said $V_R^o$ over said $V_S^o$ to obtain $Q_I(Q_I=V_R^o/V_S^o)$;

(i) continuously calculating S, $S_S$, and $S_I$ from the measured values of Q and $Q_I$ and $Q_0$, $Q_1$ and $Q_S^o$ values retrieved from erasable memory;

(j) storing in permanent memory a constant value $\Delta I$ representing a tolerance between the measured $S_I$ (calculated directly from $Q_I$) and the calculated new $S_I$ or $S_I^*$;

(k) continuously calculating $S_I^*$ in accordance with the formula $$S_I^* = \frac{-A_1 + \sqrt{A_1^2 + 4A_2[A_0 + A_1(S + S_S) + A_2(S^2 + S_S^2)]}}{2A_2}$$

(l) calculating the difference between $S_I$ and $S_I^*$;

(m) comparing the absolute value of the difference between $S_I$ and $S_I^*$ to the tolerance $\Delta I$; and (n) energizing an alarm after a selected time delay if the absolute value of the difference between $S_I$ and $S_I^*$ exceeds the tolerance $\Delta I$.

8. In a gas measurement apparatus employing a sample chamber, a reference cell and a vacuum cell to obtain a $V_R/V_S$ measurement, a standard cell for calibration and a computer, the method of checking for shifts in $Q_A^o$ and $Q_S^o$ comprising:

(a) storing in nonvolatile but erasable memory $Q_A^o$ and $Q_S^o$;

(b) storing in permanent memory a tolerance $\Delta A$;

(c) storing in permanent memory a tolerance $\Delta S$;

(d) continuously measuring $Q_A$ and $Q_S$;

(e) continuously computing a new $\Delta Q_A$ according to the formula $$\Delta Q_A = Q_A - Q_A^o$$

(f) continuously computing a new $\Delta Q_S$ according to the formula $$\Delta Q_S = Q_S - Q_S^o$$

(g) continuously comparing $\Delta Q_S$ with $\Delta S$ stored and comparing $\Delta Q_A$ with $\Delta A$ stored; and (h) continuously correcting $Q_A^o$ and $Q_S^o$ by $\Delta Q_A$ and $\Delta Q_S$, respectively, in erasable memory if either $\Delta Q_S$ or $\Delta Q_A$ exceeds the tolerances.

9. In a gas measurement apparatus employing a sample chamber, a reference cell and a vacuum cell to obtain $V_R/V_S$ measurement, a standard cell for calibration and a computer having erasable memory and permanent memory, the method of continuously self-calibrating the S-curve as components change with aging, temperature, and other causes, comprising:

(a) storing $A_0$, $A_1$, $A_2$, $\Delta A$, $\Delta S$, $K_1$, and $K_2$ in permanent memory;

(b) storing $Q_0$, $Q_1$, $Q_S^o$, and $Q_A^o$ in nonvolatile but erasable memory;

(c) continously measuring and calculating $Q_A$ and $Q_S$;

(d) continuously computing $\Delta Q_A$ according to the formula $\Delta Q_A = Q_A - Q_A^o$;

(e) continously computing $\Delta Q_S$ according to the formula $\Delta Q_S = Q_S - Q_S^o$;

(f) continously comparing $\Delta Q_A$ with $\Delta A$ stored;

(g) continously comparing $\Delta Q_S$ with $\Delta S$ stored;

(h) if either $\Delta Q_A$ or $\Delta Q_S$ exceeds the tolerance $\Delta A$ or $\Delta S$ respectively, continuously computing $\Delta Q_0$ according to the formula $$\Delta Q_0 = \left(\frac{K_1}{K_1 - K_2}\right) \Delta Q_S - \left(\frac{K_2}{K_1 - K_2}\right) \Delta Q_A$$

(i) if either $\Delta Q_A$ or $\Delta Q_S$ exceeds the tolerance $\Delta A$ or $\Delta S$ respectively, continuously computing $\Delta Q_1$ according to the formula $$\Delta Q_1 = \left(\frac{K_1 - 1}{K_1 - K_2}\right) \Delta Q_S - \left(\frac{K_2 - 1}{K_1 - K_2}\right) \Delta Q_A$$

(j) algebraically adding calculated $\Delta Q_A$ from stored $Q_A{}^o$ to obtain $Q_A{}^{o,\ new}$ and store the result in erasable memory;

(k) algebraically adding calculated $\Delta Q_S$ from stored $Q_S{}^o$ to obtain $Q_S{}^{o,\ new}$ and store the result in erasable memory;

(l) continuously calculating $Q_0{}^{new}$ according to the formula $$Q_0{}^{new} = Q_0 + \Delta Q_0$$

(m) continuously calculating $Q_1{}^{new}$ according to the formula $$Q_1{}^{new} = Q_1 + \Delta Q_1$$

(n) erasing from memory the prior values of $Q_0$, $Q_1$, $Q_A{}^o$, and $Q_S{}^o$ and substituting the values of $Q_0{}^{new}$, $Q_1{}^{new}$, $Q_A{}^{o,\ new}$, and $Q_S{}^{o,\ new}$; and (o) continuously calculating S values from measured Q values using $Q_0{}^{new}$ and $Q_1{}^{new}$ according to the formula $$S = (Q - Q_0{}^{new})/(Q_1{}^{new} - Q_0{}^{new})$$

10. In a gas measurement apparatus employing a sample chamber, a reference cell and a vacuum cell to obtain a $V_R/V_S$ measurement, a standard cell for calibration and a computer, the method of calculating the partial pressure of the gas comprising:

(a) storing in permanent memory the values of $A_0$, $A_1$ and $A_2$ representing the S calibration curve;

(b) continuously measuring, correcting, and storing in erasable memory $Q_0$ and $Q_1$;

(c) continuously computing Q from the formula $Q = V_R/V_S$ (d) continuously calculating S from the formula $$S = (Q - Q_0)/(Q_1 - Q_0)$$

(e) calculating the partial pressure of the gas from the formula $$p\mathrm{CO}_2(\mathrm{mmHg}) = A_0 + A_1 S + A_2 S^2$$

(f) and delivering the result to an intelligible display device.

* * * * *